United States Patent
Pagan et al.

(10) Patent No.: US 9,623,138 B2
(45) Date of Patent: Apr. 18, 2017

(54) SYSTEMS AND METHODS FOR SURFACE DECONTAMINATION

(71) Applicants: Lifeloc Technologies, Inc., Wheat Ridge, CO (US); AquiSense Technologies, Walton, KY (US)

(72) Inventors: Jennifer Godwin Pagan, Charlotte, NC (US); Edward Brittain Stokes, Charlotte, NC (US); John Robert Krause, Charlotte, NC (US); Paolo Batoni, Charlotte, NC (US); Gurumurthi Ravishankar, Englewood, CO (US); Kelly Silverman, Kettering, OH (US)

(73) Assignees: Lifeloc Technologies, Inc., Wheat Ridge, CO (US); AquiSense Technologies LLC, Walton, KY (US)

( * ) Notice: Subject to any disclaimer, the term of this patent is extended or adjusted under 35 U.S.C. 154(b) by 0 days.

(21) Appl. No.: 14/828,178

(22) Filed: Aug. 17, 2015

(65) Prior Publication Data
US 2016/0045633 A1    Feb. 18, 2016

Related U.S. Application Data

(60) Provisional application No. 62/037,793, filed on Aug. 15, 2014.

(51) Int. Cl.
*A61L 2/00* (2006.01)
*G01N 23/00* (2006.01)
(Continued)

(52) U.S. Cl.
CPC ...... *A61L 9/20* (2013.01); *A61L 2/10* (2013.01); *G02B 5/0891* (2013.01)

(58) Field of Classification Search
CPC .............. A61L 2/00; A61L 9/18; A61L 9/20
(Continued)

(56) References Cited

U.S. PATENT DOCUMENTS 3,941,670 A * 3/1976 Pratt, Jr. ............... A23L 3/26
                                                204/157.61
8,481,970 B2    7/2013 Cooper et al.
(Continued)

OTHER PUBLICATIONS

"Household and Travel Portable Deep Ultraviolet LED Toothbrush Sanitizer," Alibaba.com, http://www.alibaba.com/product-detail/Household-and-Travel-Porta . . . Deep Ultraviolet-60231184568.html?spm=a2700.7724857.35.1.zhVEwD, 5 pages.
(Continued)

*Primary Examiner* — Monzer R Chorbaji
(74) *Attorney, Agent, or Firm* — Holzer Patel Drennan

(57) ABSTRACT

Implementations disclosed herein provide systems and methods of automatically sterilizing a portable electronic device with ultraviolet (UV) radiation. In one implementation, the method includes distributing UV light substantially uniformly across an intended surface of a device in an enclosure, and sterilizing the intended surface using a calculated dosage of the UV light. In another implementation, an electronic device sterilization system includes an enclosure configured to selectively receive a device for sterilization using a calculated dosage of light, wherein the enclosure includes one or more LEDs, a first reflector configured to receive and reflect the light from the LEDs, and a second reflector configured to receive the light reflected from the first reflector and distribute the light uniformly onto an intended planar surface of the device.

20 Claims, 7 Drawing Sheets

(51) Int. Cl.
  *A61N 5/00* (2006.01)
  *A61L 9/20* (2006.01)
  *G02B 5/08* (2006.01)
  *A61L 2/10* (2006.01)

(58) Field of Classification Search
  USPC .......................... 422/24; 250/455.11, 492.1
  See application file for complete search history.

(56) References Cited

U.S. PATENT DOCUMENTS

| | | |
|---|---|---|
| 8,536,541 B2 | 9/2013 | Taylor et al. |
| 8,606,981 B2 | 12/2013 | Engelhardt et al. |
| 8,964,405 B2 | 2/2015 | La Porte et al. |
| 2014/0183377 A1 | 7/2014 | Bettles et al. |

OTHER PUBLICATIONS

International Searching Authority, International Search Report and Written Opinion, Nov. 18, 2015, 12 pages.

* cited by examiner

VIEW A-A

SYSTEMS AND METHODS FOR SURFACE DECONTAMINATION

The present application claims priority to pending U.S. Provisional Patent Application 62/037,793, entitled "Automatic Surface Disinfection Device For Portable Electronics," filed on Aug. 15, 2014, all of which is incorporated herein by reference for all is discloses and teaches.

BACKGROUND

Portable electronic devices (e.g., electronic tablets, smartphones, laptops, etc.) have exterior surfaces, including touch screens, which are exposed to microbial contamination due to frequent contact and shared use. Many portable electronics are not hermetically sealed, waterproof, or water-resistant. Therefore, the electronics may not be cleaned through liquid immersion or spray without an unacceptable risk of damage. Therefore, sterilizing portable electronics typically includes wiping the device with a cloth that is first moistened with a disinfectant liquid, such as alcohol, for example. However, regular use of such disinfecting cloths requires that a user keep a supply of the disinfecting cloths available and properly wipe the entire electronic device to fully sterilize the device. Further, the use of disposable disinfecting cloths is not particularly environmentally sustainable.

SUMMARY

Implementations described and claimed herein provide systems and methods of automatically sterilizing a portable electronic device with ultraviolet (UV) radiation. In one implementation, the method includes distributing UV light substantially uniformly across an intended surface of a device in an enclosure, and sterilizing the intended surface using a calculated dosage of the UV light. Substantially uniformly can be defined as less than 1% deviation in UV intensity across the intended surface.

In another implementation, an electronic device sterilization system includes an enclosure configured to selectively receive a device for sterilization using a calculated dosage of light, wherein the enclosure includes one or more light-emitting diodes (LEDs), a first reflector configured to receive and reflect the light from the LEDs, and a second reflector configured to receive the light reflected from the first reflector and distribute the light uniformly onto an intended planar surface of the device.

This Summary is provided to introduce an election of concepts in a simplified form that are further described below in the Detailed Description. This Summary is not intended to identify key features or essential features of the claimed subject matter, nor is it intended to limit the scope of the claimed subject matter. Other features, details, utilities, and advantages of the claimed subject matter will be apparent from the following more particular written Detailed Description of various implementations as further illustrated in the accompanying drawings and defined in the appended claims.

DETAILED DESCRIPTION

The technology disclosed herein includes systems and methods of decontaminating an intended surface of a device with an efficient optical design. More specifically, the technology may include an enclosure, which employs one or more compact ultraviolet (UV) point sources (e.g., light-emitting diodes (LEDs)), which are embedded in a fixture such that the UV point sources are arranged to irradiate the intended surface of the device (e.g., a portable electronic device). The UV light exposure decontaminates the surface of the device.

The disclosed technology includes a broadly defined application of surface decontamination. The term "decontamination" is defined by, refers to, and includes decontamination, sterilization, and/or disinfection of surfaces. For purposes of this disclosure, the following implementations and claims refer to the application of "sterilization" only by example but may include any sterilization, decontamination, and/or disinfection applications. For example, in some implementations, sterilization may be accomplished by killing microbes and spores. In another example, disinfection may be accomplished by inactivating viruses, or partially inactivating (e.g., 99.9%) viruses.

Figure 1:
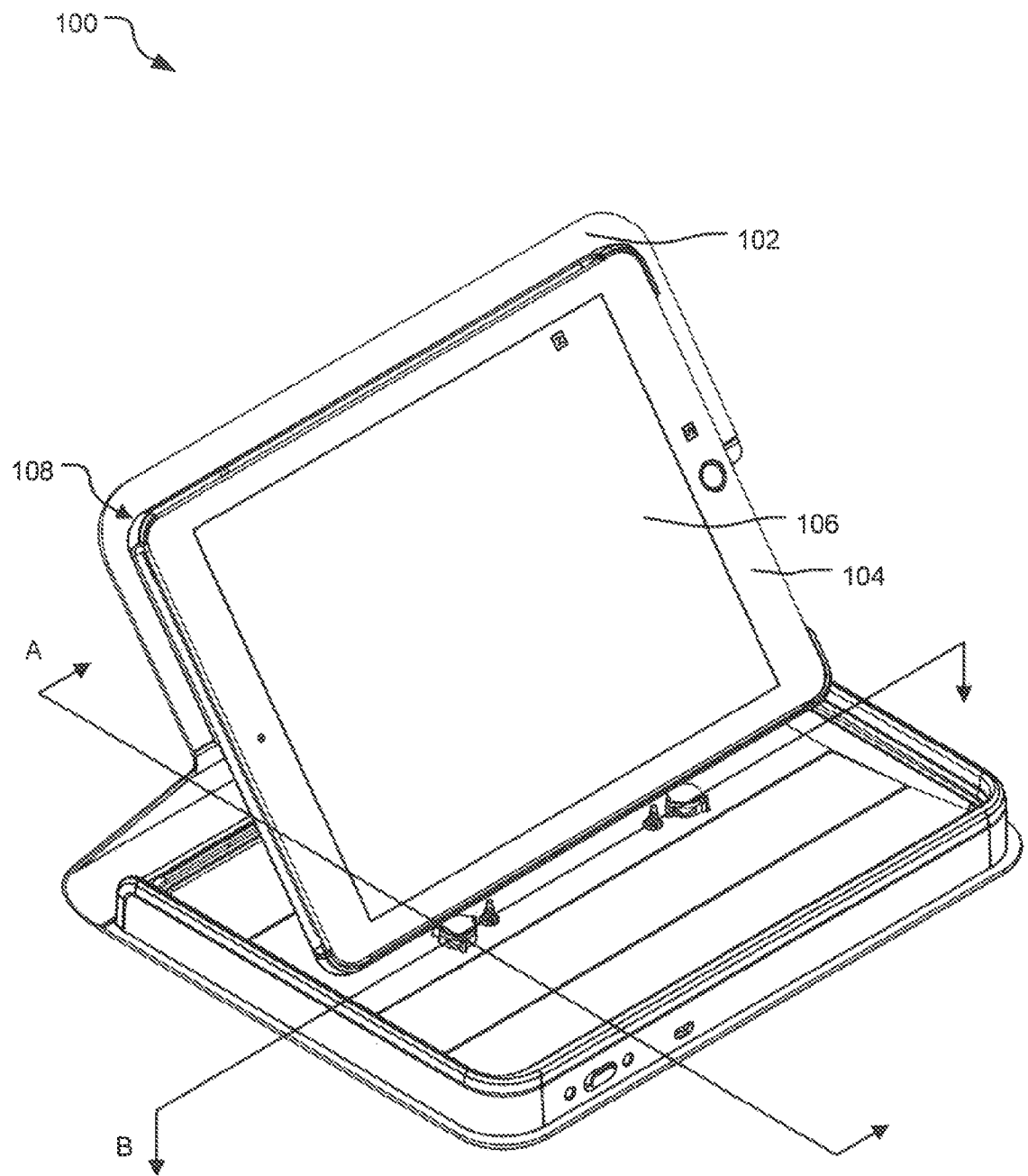
FIG. 1 is a perspective view of an example sterilization system.

FIG. 1 is a perspective view of an example sterilization system 100 for irradiating an intended surface 106. A portable electronic device 104 is shown attached to an enclosure 102. In another orientation of the enclosure 102, the device 104 is encompassed within the enclosure 102. A fixture 108 secures the portable electronic device 104 to the enclosure 102. The portable electronic device 104 may be any electronic device (e.g., a tablet or a phone). In other implementations, the device 104 can be another kind of device or object requiring sterilization.

The enclosure 102 sterilizes the intended surface 106 (e.g., a touchscreen) on the portable electronic device 104 by distributing light from an optical design incorporated within the enclosure 102. The light is distributed substantially uniformly across the intended surface 106 of the portable electronic device 104. In FIG. 1, the intended surface 106 is a planar surface, but other implementations may incorporate an intended surface with one or more curvatures and/or planar surfaces.

The light (e.g., UV light) is emitted from one or more UV point sources (not shown) and may be of various wavelengths, such as short wavelength UV (UV-C) or germicidal UV. UV light can be used to decontaminate a surface, for example, by disinfecting or sterilizing by inactivating viruses or killing microbes and spores of microorganisms (e.g., *E. coli*, etc.), respectively.

The sterilization system 100 can irradiate the intended surface 106 using a calculated UV dosage to kill or inactivate microorganisms on the intended surface 106. The calculated UV dosage can be based on several parameters, including the length of time a microorganism is exposed to UV light, the intensity and wavelength of the UV radiation, the presence of particles that can protect the microorganisms from UV light, and a microorganism's ability to withstand UV light during exposure. Depending on the potential microorganisms targeted, the parameters can vary. For example, for a specifically designed enclosure 102, in order to substantially uniformly sterilize a planar surface of the touch screen of a tablet, the UV light is emitted at a wavelength less than 290 nm for 20-30 minutes in order to irradiate the microorganisms. In another example, the wavelength and length of wavelength emission time can be more than 290 nm and/or more or less than a range of 20-30 minutes.

The enclosure 102 is operated by a control circuit (not shown, described in further detail with reference to FIG. 7) and a power source (e.g., a battery, an AC/DC power supply, a USB power source, the electronic device itself that is undergoing sterilization, etc.). The control circuit may provide an interlock (e.g., Hall effect sensor) where the one or more UV point sources do not power on unless a condition is met, such as closure of the enclosure 102. The Hall effect sensor on the circuit can be aligned to a magnet when the portable electronic device 104 is in a correct position relative to the UV sources. The magnet triggers the Hall effect sensor which communicates a signal to the circuit to turn on the LEDs, for example.

Figure 2:
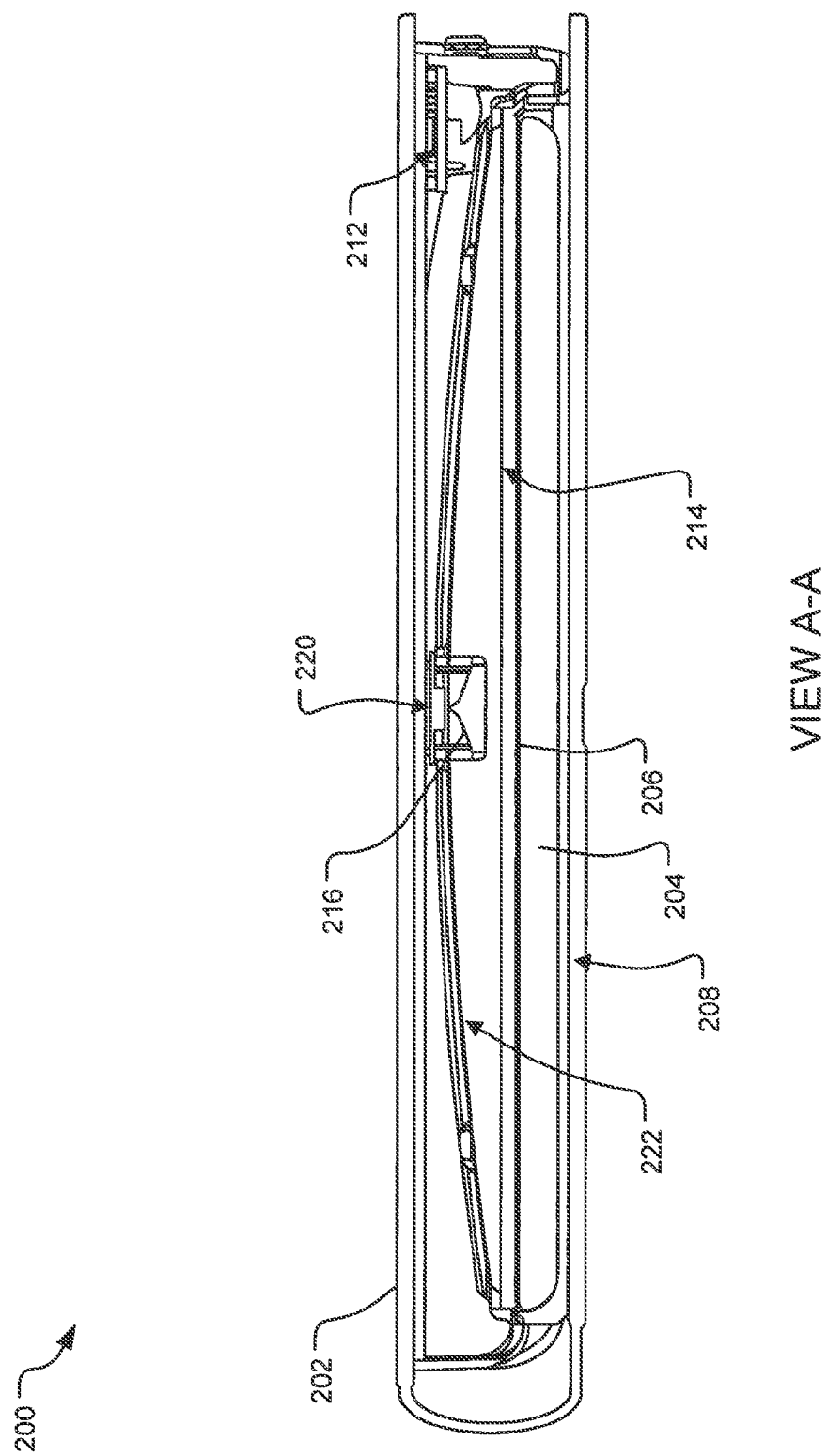
FIG. 2 is a first cross-sectional view A-A of the example sterilization system of FIG. 1.

FIG. 2 is a first cross-sectional view A-A of the example sterilization system 100 of FIG. 1. A portable electronic device 204 is shown inside an enclosure 202. A fixture 208 secures the portable electronic device 204 inside the enclosure 202. The portable electronic device 204 may be any electronic device (e.g., a tablet or a phone). In other implementations, the device 204 can be another kind of device or object requiring sterilization.

System 200 is operated by a control circuit housed in an electronic control system 212. The enclosure 202 includes an efficient optical design, which includes one or more UV point sources (e.g., LED 220) and reflectors (e.g., first reflector 216 and second reflector 222). In this cross-sectional view, only one LED 220 is shown.

The reflectors can be made of any light-reflecting material (e.g., refractory material, mirror substrates including borosilicate glass or UV fused silica, etc.). The reflectors can also vary in size and shape. For example, in one implementation, the first reflector 216 is substantially conical shaped, and the second reflector 222 is concave shaped.

The enclosure 202 sterilizes an intended surface 206 of the portable electronic device 204 by emitting UV light from the LED 220 onto the first reflector 216. The UV light reflects from the first reflector 216 onto the second reflector 222. The second reflector 222 is larger than the first reflector 216. In other implementations, the number, sizes, and locations of the reflectors can vary, as well as the locations of the UV point sources.

The UV light is reflected off the second reflector 222 and distributed substantially uniformly across an intended surface 206 of the portable electronic device 204. In some implementations, such as in FIG. 2, the UV light is emitted through a UV transmitting material or shield 214 and onto the intended surface 206 of the portable electronic device 204. In implementations utilizing a UV transmitting material 214, the UV light is filtered before it reaches the intended surface 206. The UV transmitting material 214 can be made of a variety of materials (e.g., sapphire, quartz, polymethyl methacrylate, $CaF_2$, $MgF_2$, $BaF_2$ and UV fused silica, etc.).

There can be other various optical designs in the disclosed technology. In another implementation, there can be one or more LEDs incident flux with various radiation patterns optimized through die shaping and/or secondary reflective and/or refractive optics to maximize flux and dose uniformity at the intended surface 206 to be disinfected. The LEDs can be mounted either on the inside front cover of the enclosure 202 or on the same side of the enclosure 202 where the portable electronic device 204 is held.

In another implementation, there can be one or more LEDs with various radiation patterns irradiating a reflective surface located on one or more of the following locations: reflective material located on the inside front cover of the enclosure 202, reflective material located on a beveled edge attached to the front cover or the device side of the enclosure 202, and reflective material around the perimeter of the device side of the enclosure 202.

In another implementation including one or more LEDs, an irradiation pattern is produced via multiple reflections from multiple reflectors. A multitude of reflected rays of UV light across the surface of the device 204 can be produced, as defined by using Snell's law.

The light from one of more LEDs is both refracted and reflected, "bouncing" off the intended surface 206 onto some other reflective surface, such as larger reflector 222, creating the irradiation pattern. Because the intended surface 206 is a partially transparent medium, the light waves are refracted which is defined by Snells law.

In another implementation including one or more LEDs, an irradiation pattern is produced by projecting the LED emission onto the first reflector 216 which in turn projects the light onto a second, larger reflector 222. The light reflected off the second, larger reflector 222 can then impinge on the intended surface 206 of the device 204.

In another implementation including one or more LEDs, an irradiation pattern is produced by projecting the LED emission onto the first reflector 216, which in turn projects the light onto the second, larger reflector 222. The light reflected off the second, larger reflector 222 can then travel through a UV transmitting material 214 (e.g., sapphire, quartz, polymethyl methacrylate, $CaF_2$, $MgF_2$, $BaF_2$ and UV fused silica) before impinging on the intended surface of a device.

The UV transmitting material 214 may have surface structures or patterns to act as a diffuser for the UV light. The UV transmitting material 214 may also have areas which are patterned with a reflective material, which reflects a portion of the incident light back onto the second, larger reflector or the material itself could reflect a portion of the incident light back onto the second, larger reflector 222 creating an integrating chamber to further homogenize the light incident on the intended surface of the device 204.

Figure 3:
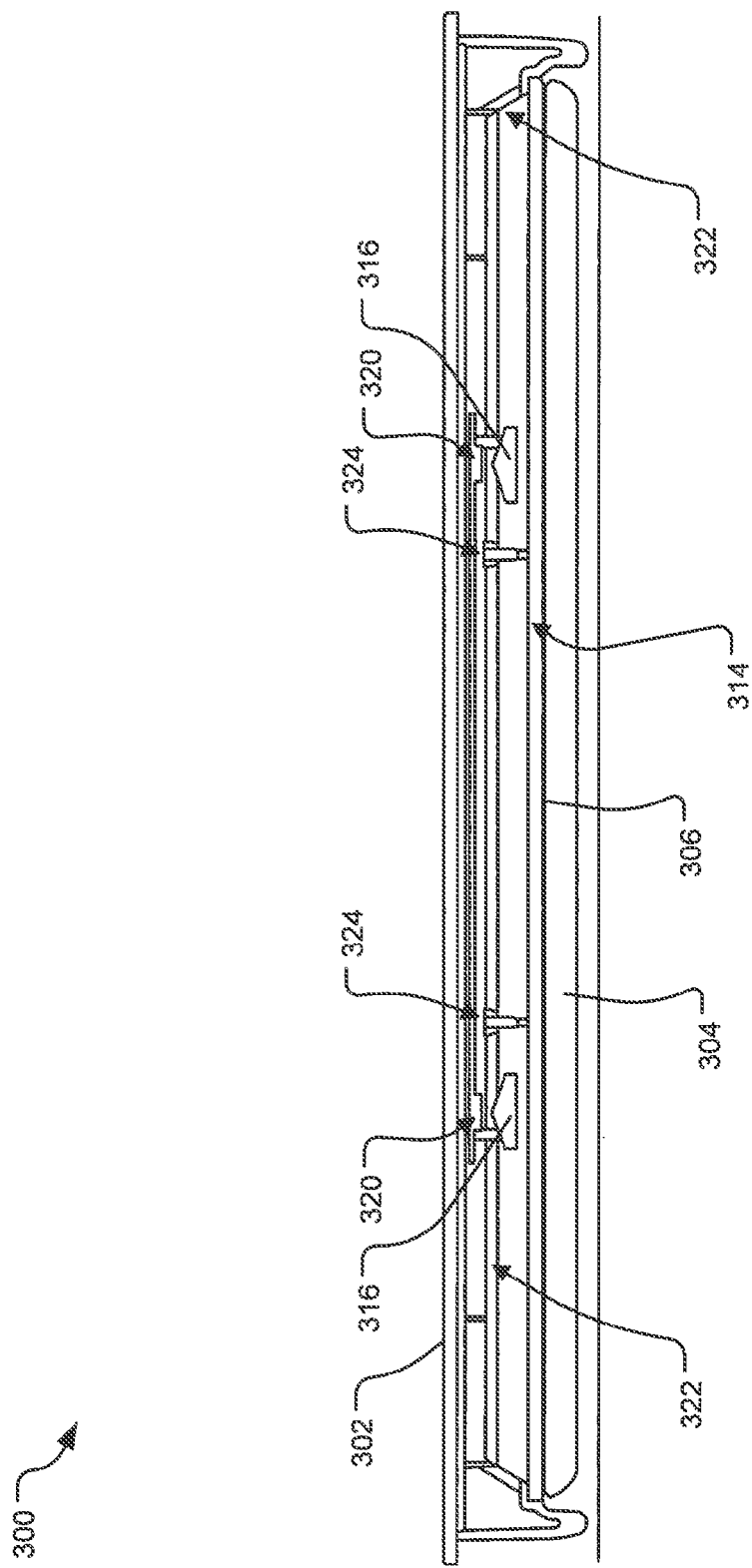
FIG. 3 is a second cross-sectional view B-B of the example sterilization system of FIG. 1.

FIG. 3 is a second cross-sectional view B-B of the example sterilization system 100 of FIG. 1. A portable electronic device 304 is shown inside an enclosure 302. The enclosure 302 includes an efficient optical design, which includes one or more UV point sources (e.g., LEDs 320) and reflectors (e.g., a first reflector 316 and a second reflector 322). In this cross-sectional view, two LEDs 320 are shown.

The reflectors 316, 322 can be any light reflecting material (e.g., refractory material, mirror substrates including borosilicate glass or UV fused silica, etc.). The reflectors 316, 322 can also vary in size, shape, and angles of their surfaces. For example, in one implementation, the first reflector 316 is substantially conical shaped, and the second reflector 322 is concave shaped.

The enclosure 302 sterilizes an intended surface 306 of the portable electronic device 304 by emitting UV light from the LEDs 320 onto the first reflector 316. The UV light reflects from the first reflector 316 onto the second reflector 322. The second reflector 322 is larger than the first reflector 316. In other implementations, the number, sizes, and locations of the reflectors can vary, as well as the locations of the UV point sources.

The UV light is reflected off the second reflector 322 and distributed substantially uniformly across an intended surface 306 of the portable electronic device 304. In some implementations, such as in FIG. 3, the UV light is emitted through a UV transmitting material 314 and onto the intended surface 306 of the portable electronic device 304. In implementations utilizing a UV transmitting material 314, the UV light is filtered before it reaches the intended surface 306. The UV transmitting material 314 can be made of a variety of materials (e.g., sapphire, quartz, polymethyl methacrylate, $CaF_2$, $MgF_2$, $BaF_2$ and UV fused silica, etc.).

FIG. 3 also illustrates two stand-offs 324, which provide mechanical stability so that UV transmitting material 314 cannot be flexed into any optical components, such as the first reflector 316 and second reflector 322. The stand-offs 324 can be made of a variety of materials (e.g., acrylic). In other implementations, there may be more one or more than two depicted stand-offs within the enclosure 302, or otherwise none.

Figure 4:
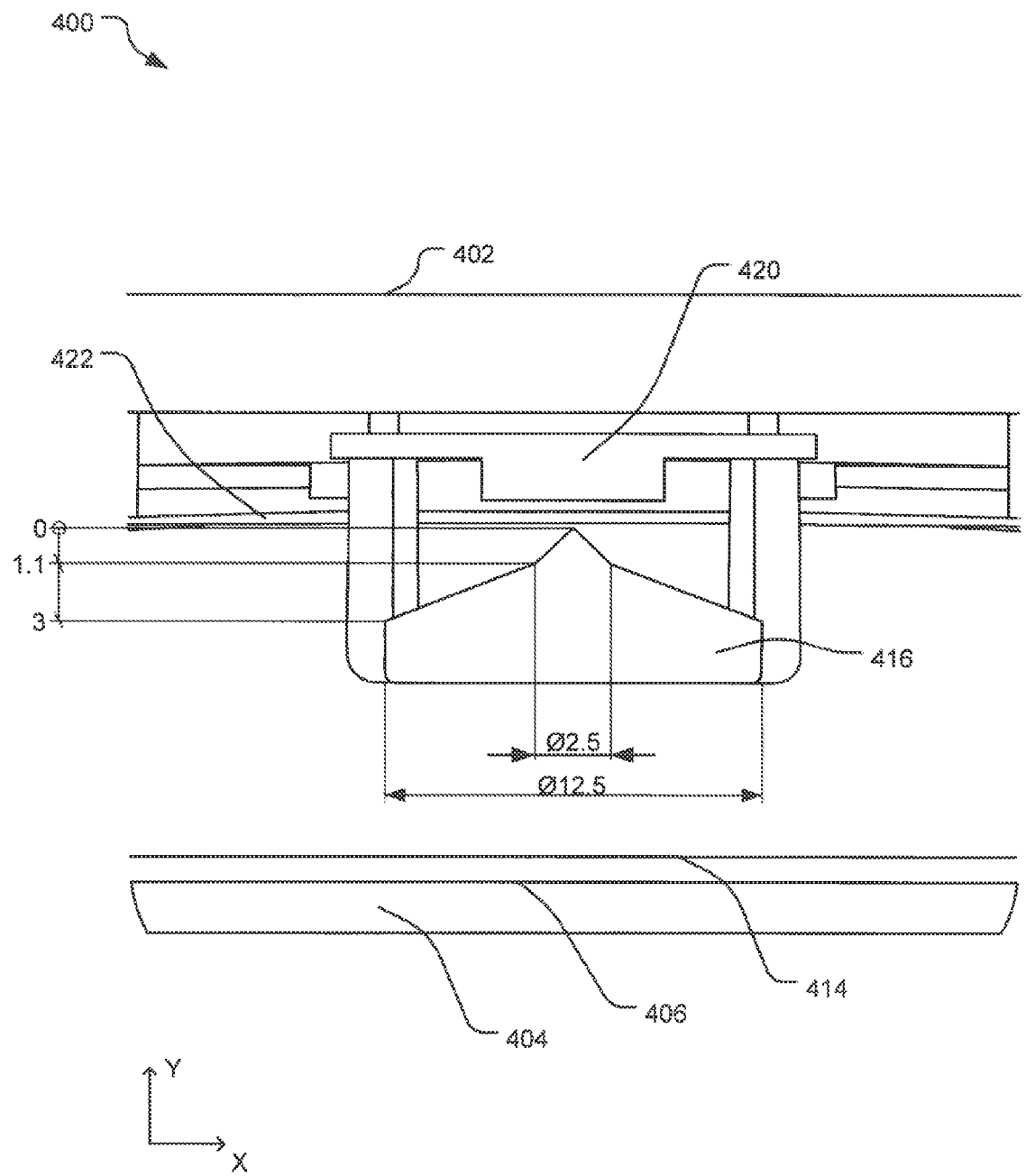
FIG. 4 is a partial cross-sectional detail view of an example sterilization system.

FIG. 4 is a partial cross-sectional detail view of an example sterilization system 400. This partial, enlarged view shows the efficient optical design in the enclosure 402. There is a UV point source (e.g., LED 420) and reflectors (e.g., a first reflector 416 and a second reflector 422). In this implementation, an irradiation pattern is produced by projecting the LED 420 emission onto the first reflector 416, which in turn projects the UV light onto the larger second reflector 422. The light reflected off the larger second reflector 422 can distribute on the intended surface 406 of an electronic portable device 404. In some implementations, such as in FIG. 4, the UV light is emitted through a UV transmitting material 414 and onto the intended surface 406 of the portable electronic device 404.

The measurements of the optical design sterilization system 400 may vary depending on the size and dimensions of the intended surface 406, for example. Example measurements are shown in the implementation in FIG. 4. The outer diameter of the first reflector 416 is approximately 12.5 nm, with an intermediate diameter of approximately 2.5 nm, as noted in FIG. 4. The first reflector 416 has a symmetrically multi-angled reflective surface. In this implementation, the reflective surface of the first reflector 416 has four different angles (e.g., approximately 45°, −45°, 20°, and −20° with respect to the planar intended surface 406), which are described in more detail below. In other implementations, the surfaces of both the first reflector 416 and second reflector 422 may have other angles and dimensions.

The first reflector 416 has a conical peak portion located in the reflective center area of the first reflector 416, marked as the area measuring from 0 to 1.1 nm in height on a y-axis, and 2.5 nm wide on an x-axis. The slope of the top surface of the conical peak portion symmetrically increases from both ends of the first reflector 416 at approximately 45° from one side (e.g., the left side in FIG. 4) and approximately −45° from the other side (e.g., the right side in FIG. 4) and is constant until the slopes meet at a peak in the center of the first reflector 416.

The symmetrical reflective surface area portions on the sides of the conical peak portion (e.g., the left and right sides in FIG. 4) of the first reflector 416 measure approximately 5 nm from each end to the conical peak portion on an x-axis. The slopes of the symmetrical top surface area portions from both ends to the conical peak portion is constant at approximately 20° from one side (e.g., the left side in FIG. 4) and approximately −20° from the other side (e.g., the right side in FIG. 4).

Due to the symmetrically multi-angled top surface of the first reflector, the UV light can be transmitted from the LED 420 to the first reflector 416 and reflected onto a second reflector 422, and distributed uniformly across an intended surface 406.

Figure 5:
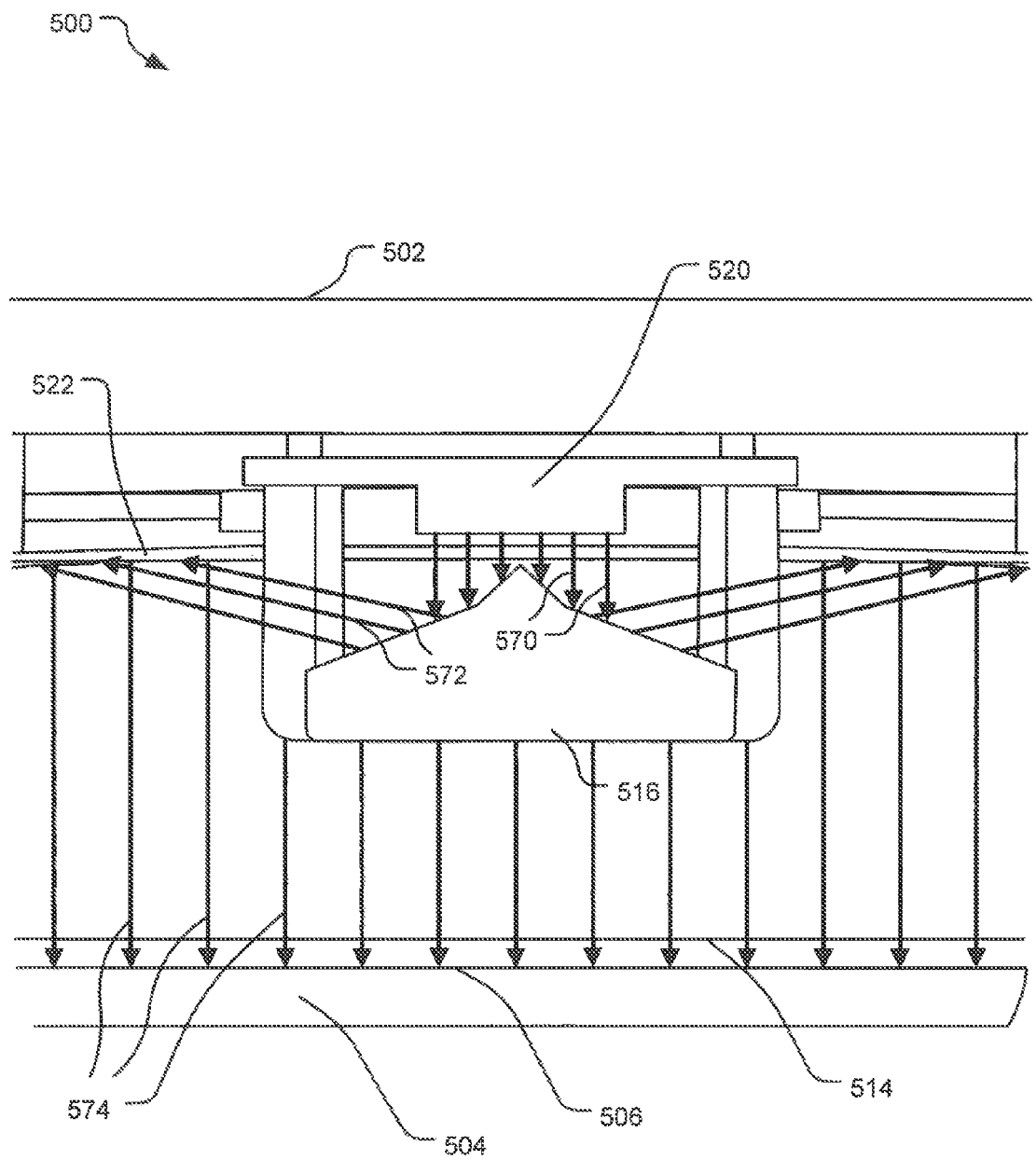
FIG. 5 is a partial cross-sectional detail view of an example sterilization system showing UV ray transmission paths.

FIG. 5 is a partial cross-sectional detail view of an example sterilization system 500 showing UV ray transmission paths. A portable electronic device 504 is shown inside an enclosure 502. The enclosure 502 includes one or more UV point sources (e.g., LED 520) and reflectors (e.g., a first reflector 516 and a second reflector 522). In this cross-sectional view, one LED 520 is shown.

The enclosure 502 sterilizes an intended surface 506 of the portable electronic device 504 by emitting UV light from the LED 520 onto a first reflector 516, as shown by UV ray transmission paths 570. The UV light reflects from the first reflector 516 onto a second reflector 522, as shown by UV ray transmission paths 572. The second reflector 522 is larger than the first reflector 516.

The UV light is reflected off the second reflector 522 and distributed substantially uniformly across an intended surface 506 of the portable electronic device 504, as shown by UV ray transmission paths 574. In some implementations, such as in FIG. 5, the UV light is emitted through a UV transmitting material 514 and onto the intended surface 506 of the portable electronic device 504. In implementations utilizing a UV transmitting material 514, the UV light is filtered before it reaches the intended surface 506. The UV transmitting material 514 can be made of a variety of materials (e.g., sapphire, quartz, polymethyl methacrylate, $CaF_2$, $MgF_2$, $BaF_2$ and UV fused silica, etc.). As shown by the multiple UV ray transmission paths 574, light can be uniformly distributed to irradiate an entire planar surface of an electronic portable device.

In other implementations, the number, sizes, locations, and the angles of the surfaces of the reflectors can vary, as well as the locations of the one or more UV point sources. The optical design configuration can be specifically tailored to the intended decontamination use.

Figure 6:
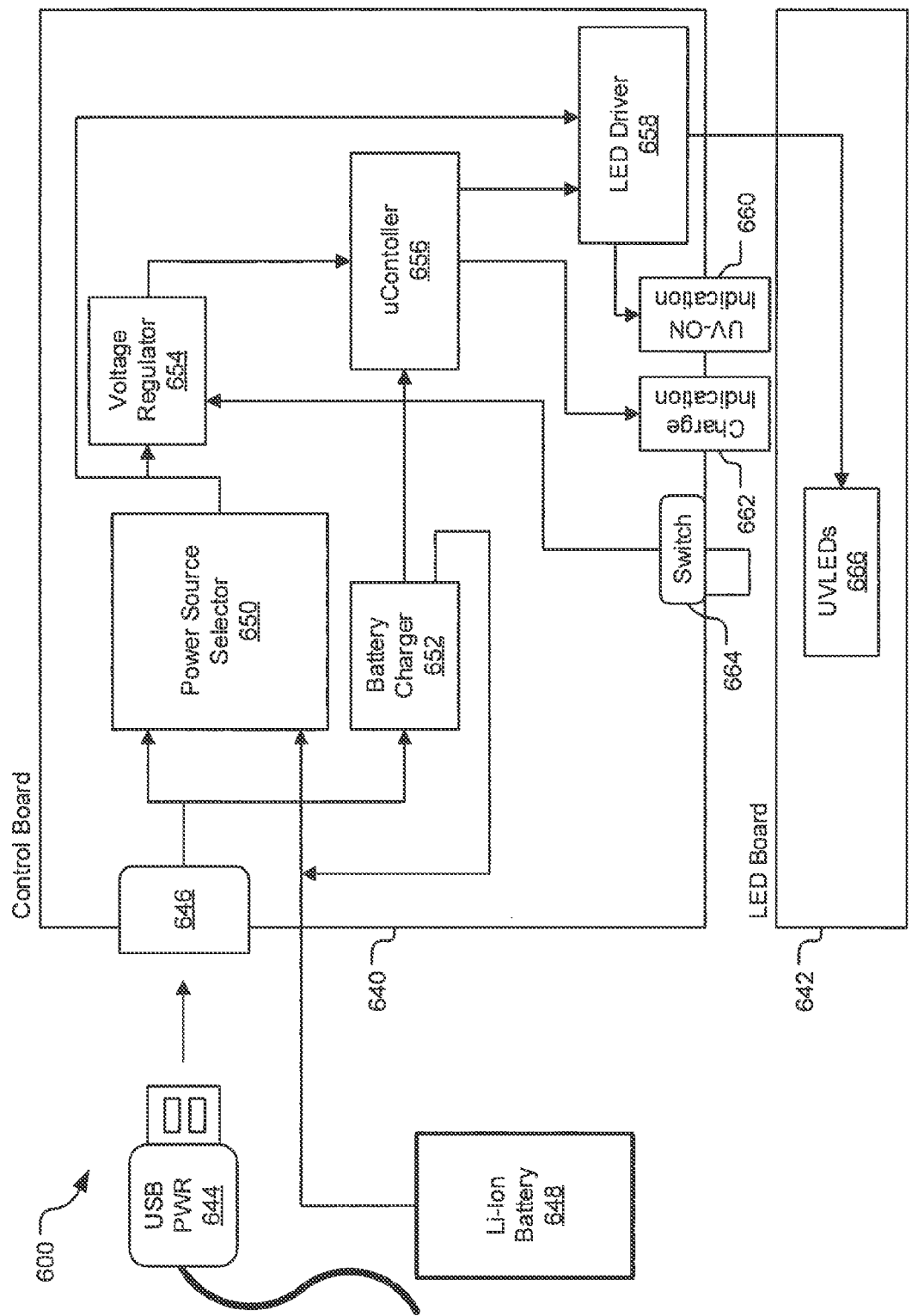
FIG. 6 is a circuit diagram of an example sterilization system.

FIG. 6 is a block diagram of an electronic circuit 600 in an example sterilization system. The electronic circuit 600 mechanically supports and electrically connects electronic components in a sterilization system. The electronic circuit 600 includes power sources (e.g., a USB 644 via a USB power port 646, a battery 648, etc.), a control board 640, and an LED board 642. Power is provided to the sterilization system by a power source. A power source selector 650 can select the power source. If a battery 648 is used for power, the battery 648 may be rechargeable by a battery charger 652 located on the control board 640. For example, compact rechargeable battery sources such as lithium ion, lithium polymer or metal halide batteries can be used to power the circuit 600, have a recharge circuit, and plug into the control board 640. In FIG. 6, a lithium battery 648 and a USB power source 644 are shown to power the control board 640.

The power source can be provided by a user or selected by a power source selector 650 upon system need. For example, a user can turn a switch 664 on the control board 640 to power on the control circuit 600. In another example, power is provided automatically via a connected power source.

A voltage regulator 654 is located on the control board 640 and regulates the voltage provided from the power source. The power is provided to a microcontroller 656 and an LED driver 658 on the control board 640.

The microcontroller 656 can send signals to indicator lights on the control board 640. For example, if the electronic circuit 600 is charging the battery 648, the microcontroller 656 signals a charge indication light 662 to illuminate and blink to let the user know that the battery 648 is charging. Or, the charge indication light 662 can illuminate to indicate that the battery 648 is low and needs to be recharged. In another example, a UV-ON indication light 660 can illuminate to indicate that the UV source power is on, for example, by a continuous wave mode blue LED or pulsed mode blinking LED. Or, in another example, the UV-ON indication light 660 can be a plurality of LED indicator lights, where the number of illuminated lights is an indication of the duration of time for which the UV source has been on.

The LED Driver 658 on the control board 640 communicates with one or more UV point sources (e.g., LEDs 666) on the LED Board 642 to turn the LEDs 666 on and off for light emission operations.

In another implementation, the electronic circuit 600 may have an automatic on/off switching capability (e.g., an interlock). The interlock is used to ensure a user is shielded from any UV radiation. In one implementation, the UV transmitting operations do not take place unless the enclosure is closed and the interlock activated. The interlock may use a physical or optical design to connect the electronic circuit 600. An optical example is a photodiode or infrared sensor where examples of a physical design include a Hall effect sensor, an electrical contact, or a reed switch. The interlock is activated when the cover of the enclosure is closed.

In another implementation, the electronic circuit 600 may have a timer program for UV point sources. For example, the electronic circuit 600 operates the UV point sources in a pulsed mode to reduce the need for cooling design. A timer circuit measures when the UV point sources should turn off (i.e., the cycle is complete). The UV point sources are on long enough to deliver a sufficient calculated dose of UV light to sterilize an intended surface per the incident flux provided by the optical design portion of the system. The calculated dosage can be based on one or more parameters, including the length of time a microorganism is exposed to UV light, the intensity and wavelength of the UV radiation, the presence of particles that can protect the microorganisms from UV light, and a microorganism's ability to withstand UV light during exposure. In one implementation, the calculated dose is determined by the following equation: dose (mJ/cm$^2$)=incident flux (mW/cm$^2$)×UV point source on time (seconds). For example, the incident flux range may be approximately 1000-100,000 mW S/cm$^2$.

Figure 7:
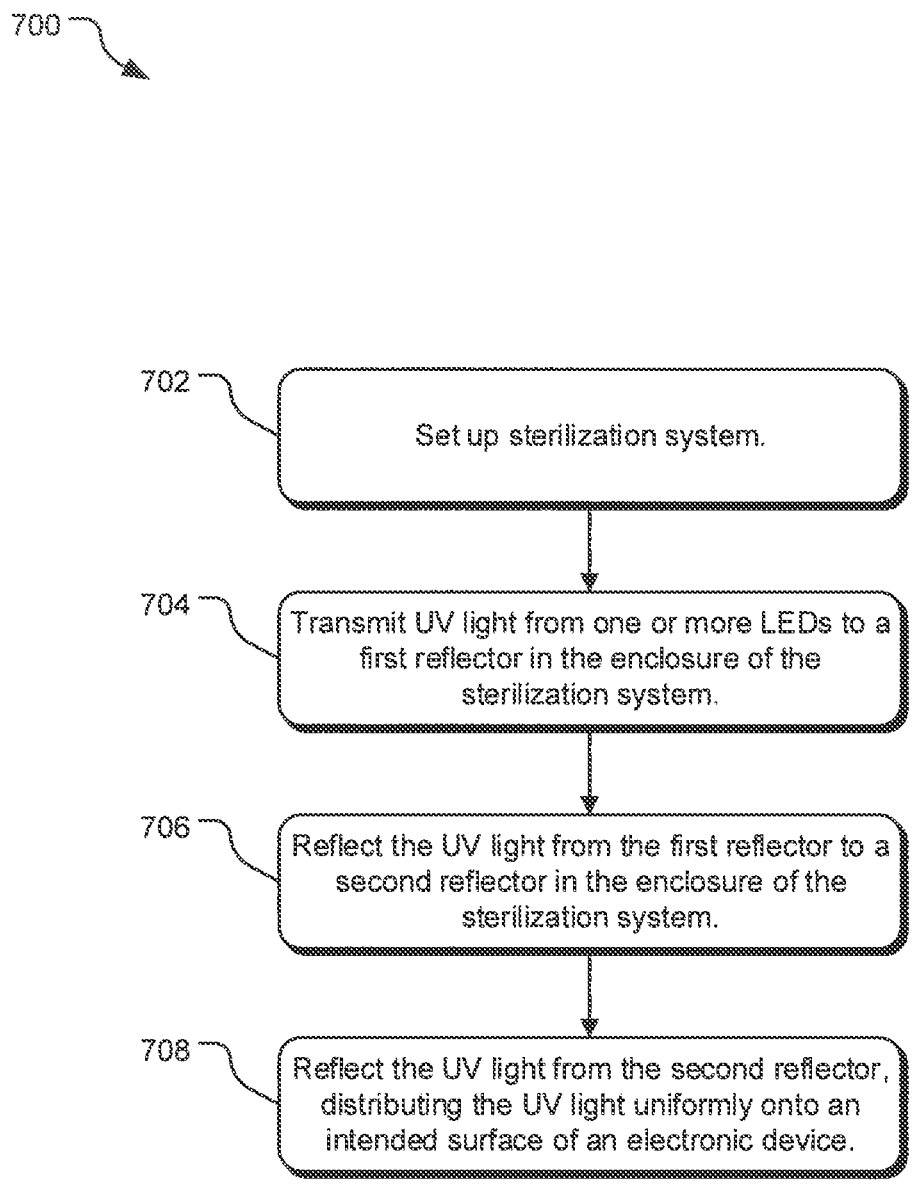
FIG. 7 shows example operations of sterilizing an intended surface with an example sterilization system.

FIG. 7 shows operations of sterilizing an intended surface with the disclosed technology. A set up operation 702 includes the placement and securing of the electronic device in the enclosure. For example, is a user wants to clean an electronic a device, such as a phone or tablet, the user can insert the electronic device into the disclosed enclosure. Once the electronic device is secured in the enclosure, the enclosure can be closed. The enclosure can be activated to begin operations either automatically or manually. A user can push a power button or switch, or the system can begin operations automatically via an interlock.

Once the set up operation 702 occurs, an operation 704 transmits light, such as UV light, from one or more LEDs to a first reflector located in the enclosure. The UV light may be of various wavelengths, such as short wavelength UV (UV-C) or germicidal UV. In one implementation, the UV wavelength is less than 290 nm for the desired purpose of sterilizing an intended surface by killing or inactivating microorganisms by destroying their nucleic acids and disrupting their DNA. Depending on the intended use, the light is emitted according to a calculated dosage to kill a microorganism. The calculated dosage can be based on several parameters, including the length of time a microorganism is exposed to UV light, the intensity and wavelength of the UV radiation, the presence of particles that can protect the microorganisms from UV light, and a microorganism's ability to withstand UV during exposure.

The first reflector receives the UV light from the LEDs. In one implementation, the first reflector is located proximate to a first side of the one or more LEDs. However, the location of the first reflector can vary in the enclosure.

A first reflecting operation 706 reflects the UV light from the first reflector to a second reflector. In one implementation, the second reflector is located on a second side of the LEDs opposite the first side of the LEDs. However, the location of the second reflector can vary in the enclosure. In some implementations, such as those shown in FIGS. 2-4, the second reflector is larger than the first reflector. The second reflector receives the UV light from the first reflector.

A second reflecting operation 708 reflects the light from the second reflector, distributing the light onto an intended surface of the electronic device using the calculated UV dosage (e.g., based on length of time a microorganism is exposed to UV light and intensity and wavelength of the UV radiation). As a result, the efficient optical design of the disclosed portable system sterilizes substantially the entire surface of the electronic device killing or inactivating microorganisms.

The above specification, examples, and data provide a complete description of the structure and use of example implementations of the invention. Since many implementations of the invention can be made without departing from the spirit and scope of the invention, the invention resides in the claims hereinafter appended. Furthermore, structural features of the different implementations may be combined in yet another implementation without departing from the recited claims. The implementations described above and other implementations are within the scope of the following claims.

What is claimed is:

1. A method, comprising:
    transmitting ultraviolet (UV) light from a point source to a first reflector, the first reflector located proximate to a first side of the point source;
    reflecting UV light from the first reflector to a second reflector, the second reflector located proximate to a second side of the point source opposite the first side of the point source;
    reflecting UV light from the second reflector to an intended surface of a device in an enclosure, wherein the UV light is distributed,
    substantially uniformly across the intended surface of the device in the enclosure; and
    sterilizing the intended surface using a calculated dosage of the UV light.

2. The method of claim 1, wherein the calculated dosage is based on at least one of length of time of microorganism exposure to the UV light, UV intensity, and wavelength of the UV light radiation.

3. The method of claim 1, wherein the intended surface is a planar surface.

4. The method of claim 1, wherein the point source is one or more light-emitting diodes (LEDs).

5. The method of claim 1, wherein the reflected UV light from the second reflector is transmitted through a UV transmitting material located between the second reflector and the intended surface.

6. The method of claim 1, wherein the second reflector is larger than the first reflector.

7. The method of claim 1, wherein the UV light is emitted at a wavelength less than 290 nm.

8. An electronic device sterilization system comprising:
   an enclosure configured to selectively receive a device for sterilization using a calculated dosage of light, wherein the enclosure includes:
   one or more light-emitting diodes (LEDs);
   a first reflector configured to receive and reflect the light from the LEDs; and
   a second reflector configured to receive the light reflected from the first reflector and distribute the light substantially uniformly onto an intended surface of the device.

9. The electronic device sterilization system of claim 8, wherein the second reflector is larger than the first reflector.

10. The electronic device sterilization system of claim 8, wherein the light is ultraviolet (UV) light.

11. The electronic device sterilization system of claim 8, further comprising:
   a UV transmitting material located proximate to the first reflector.

12. The electronic device sterilization system of claim 8, wherein the light is emitted at a wavelength less than 290 nm.

13. The electronic device sterilization system of claim 8, wherein the first reflector is conical shaped and the second reflector is concave shaped.

14. A sterilization apparatus, comprising:
   one or more light-emitting diodes (LEDs);
   a first reflector configured to receive and reflect light from the LEDs; and
   a second reflector configured to receive the light reflected from the first reflector and reflect the light uniformly onto an intended surface for sterilization based on a calculated dosage of the light.

15. The sterilization apparatus of claim 14, wherein the light is ultraviolet (UV) light.

16. The sterilization apparatus of claim 15, further comprising a UV transmitting material located between the second reflector and the intended surface.

17. The sterilization apparatus of claim 14, wherein the first reflector and second reflector are mirror substrates including at least one of borosilicate glass and UV fused silica.

18. The sterilization apparatus of claim 14, wherein the first reflector is conical shaped.

19. The sterilization apparatus of claim 14, wherein the second reflector is concave shaped.

20. The sterilization apparatus of claim 14, wherein the UV transmitting material is at least one of sapphire, quartz, polymethyl methacrylate, $CaF_2$, $MgF_2$, $BaF_2$ and UV fused silica.

* * * * *